United States Patent
Hee-Hanson et al.

(10) Patent No.: US 12,377,226 B1
(45) Date of Patent: Aug. 5, 2025

(54) MEDICAMENT DELIVERY DEVICE

(71) Applicant: Genzyme Corporation, Cambridge, MA (US)

(72) Inventors: Alexander Hee-Hanson, Melbourn (GB); Michael Parrott, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/640,710

(22) Filed: Apr. 19, 2024

(51) Int. Cl.
    *A61M 5/32*     (2006.01)
    *A61M 5/20*     (2006.01)

(52) U.S. Cl.
    CPC ..... *A61M 5/3234* (2013.01); *A61M 2005/202* (2013.01); *A61M 2005/2073* (2013.01)

(58) Field of Classification Search
    CPC ........ A61M 5/2033; A61M 2005/2073; A61M 2005/206; A61M 2005/208
    See application file for complete search history.

(56) References Cited

U.S. PATENT DOCUMENTS

| | | |
|---|---|---|
| 2,522,961 A | 9/1950 | William |
| 2,633,267 A | 3/1953 | Lebus |
| 3,886,513 A | 5/1975 | Smith et al. |
| 4,801,295 A | 1/1989 | Spencer |
| 5,045,062 A | 9/1991 | Henson |
| 5,176,275 A | 1/1993 | Bowie |
| 5,328,484 A | 7/1994 | Somers et al. |
| 5,396,051 A | 3/1995 | Kuhn et al. |
| 5,478,316 A * | 12/1995 | Bitdinger ............ A61M 5/2033 604/157 |
| 5,505,324 A | 4/1996 | Danico |
| 5,505,706 A | 4/1996 | Maus et al. |
| 5,536,917 A | 7/1996 | Suppelsa et al. |

(Continued)

FOREIGN PATENT DOCUMENTS

| | | |
|---|---|---|
| DE | 3921747 A1 | 1/1991 |
| EP | 3501577 A1 | 6/2019 |

(Continued)

OTHER PUBLICATIONS

Needle-based injection systems for medical use requirements and test methods, Part 1: Needle injection systems, ISO 11608-1:2014(E), Third Edition, Switzerland, ISO, Dec. 15, 2014, pp. 1-13.

(Continued)

*Primary Examiner* — Laura A Bouchelle
(74) *Attorney, Agent, or Firm* — Fish & Richardson P.C.

(57) ABSTRACT

A medicament delivery device comprising a body, a needle, and an actuation member movable proximally from an initial position to a protruded position, and distally from the protruded position to an actuation position. The device has a transfer member which is movable proximally between an extended and a retracted position. In the extended position the distal end of the transfer member protrudes from the body. One of the actuation member and the transfer member has a drive slot and the other of the actuation member and the transfer member comprises a protrusion located in the drive slot. The drive slot has a circumferentially-extending portion having an abutment surface. The protrusion engages the abutment surface to move the actuation member from the initial position to the protruded position.

29 Claims, 9 Drawing Sheets

(56) References Cited

U.S. PATENT DOCUMENTS

| | | |
|---|---|---|
| 5,622,274 A | 4/1997 | Bright |
| 5,738,658 A | 4/1998 | Maus et al. |
| 5,984,899 A | 11/1999 | D'Alessio et al. |
| 6,080,461 A | 6/2000 | Wozniak et al. |
| 6,394,985 B1 | 5/2002 | Lin |
| 7,762,981 B2 | 7/2010 | Dacquay et al. |
| 7,887,506 B1 | 2/2011 | Smolyarov et al. |
| 7,918,824 B2 | 4/2011 | Bishop et al. |
| 8,133,198 B2 | 3/2012 | Neer |
| 8,409,138 B2 | 4/2013 | James et al. |
| 8,734,394 B2 | 5/2014 | Adams et al. |
| 9,044,553 B2 | 6/2015 | James et al. |
| 9,402,957 B2 | 8/2016 | Adams et al. |
| 9,872,961 B2 | 1/2018 | Fourt et al. |
| 10,118,001 B2 | 11/2018 | Fourt et al. |
| 10,314,981 B2 | 6/2019 | Sampson et al. |
| 10,350,362 B2 | 7/2019 | Dennis, Jr. et al. |
| 10,363,377 B2 | 7/2019 | Atterbury et al. |
| 11,298,462 B2 | 4/2022 | Atterbury et al. |
| 11,331,432 B2 | 5/2022 | Holmqvist et al. |
| 11,369,751 B2 * | 6/2022 | Ruan .................. A61M 5/3272 |
| 11,452,821 B2 | 9/2022 | LaFever et al. |
| 12,337,160 B1 | 6/2025 | Hee-Hanson et al. |
| 2002/0055712 A1 | 5/2002 | Neracher |
| 2004/0039336 A1 | 2/2004 | Amark et al. |
| 2005/0101919 A1 | 5/2005 | Brunnberg |
| 2005/0273061 A1 | 12/2005 | Hommann et al. |
| 2006/0224124 A1 | 10/2006 | Scherer |
| 2007/0270777 A1 | 11/2007 | Dacquay et al. |
| 2008/0097311 A1 | 4/2008 | Dacquay et al. |
| 2008/0097390 A1 | 4/2008 | Dacquay et al. |
| 2008/0269692 A1 | 10/2008 | James et al. |
| 2009/0036868 A1 | 2/2009 | Pinedjian et al. |
| 2009/0281496 A1 | 11/2009 | Matusch |
| 2010/0211005 A1 | 8/2010 | Edwards et al. |
| 2011/0054414 A1 | 3/2011 | Shang et al. |
| 2011/0144594 A1 | 6/2011 | Sund et al. |
| 2011/0202011 A1 | 8/2011 | Wozencroft |
| 2011/0319813 A1 | 12/2011 | Kamen et al. |
| 2013/0237921 A1 | 9/2013 | Lannan et al. |
| 2013/0267897 A1 | 10/2013 | Kemp et al. |
| 2014/0236076 A1 | 8/2014 | Marshall et al. |
| 2014/0249483 A1 | 9/2014 | Kiilerich et al. |
| 2014/0263156 A1 | 9/2014 | Newsom et al. |
| 2014/0276637 A1 | 9/2014 | Massey, Jr. |
| 2015/0246180 A1 | 9/2015 | Fenlon et al. |
| 2015/0273162 A1 | 10/2015 | Holmqvist |
| 2016/0001015 A1 | 1/2016 | Kucuk et al. |
| 2016/0354555 A1 | 12/2016 | Gibson et al. |
| 2016/0367763 A1 | 12/2016 | Tschirren et al. |
| 2017/0215699 A1 | 8/2017 | Ouyang et al. |
| 2017/0216526 A1 | 8/2017 | Brereton et al. |
| 2017/0224929 A1 | 8/2017 | Sampson et al. |
| 2017/0246403 A1 | 8/2017 | Cowe et al. |
| 2017/0361034 A1 | 12/2017 | Scheller et al. |
| 2018/0250471 A1 | 9/2018 | Grimoldby et al. |
| 2018/0339114 A1 | 11/2018 | Wendland et al. |
| 2019/0030249 A1 | 1/2019 | Gonzalez et al. |
| 2019/0192785 A1 | 6/2019 | Wendland et al. |
| 2019/0366000 A1 | 12/2019 | Cowe et al. |
| 2020/0114041 A1 | 4/2020 | Alas et al. |
| 2020/0316314 A1 | 10/2020 | Buri et al. |
| 2021/0077732 A1 | 3/2021 | Egelhofer |
| 2021/0196900 A1 | 7/2021 | Apply et al. |
| 2022/0015429 A1 | 1/2022 | Brown et al. |
| 2022/0176042 A1 | 6/2022 | Belisle |
| 2022/0395640 A1 | 12/2022 | Schwartzentruber |
| 2023/0001099 A1 | 1/2023 | Dunn |
| 2023/0238105 A1 | 7/2023 | Schneider et al. |
| 2023/0347074 A1 | 11/2023 | Gavin |
| 2024/0009397 A1 | 1/2024 | In et al. |

FOREIGN PATENT DOCUMENTS

| | | |
|---|---|---|
| WO | WO 2002/047746 A1 | 6/2002 |
| WO | WO 2011/109205 A2 | 9/2011 |
| WO | WO 2016/081238 A1 | 5/2016 |
| WO | WO 2019/074788 A1 | 4/2019 |
| WO | WO 2020/190529 A1 | 9/2020 |

OTHER PUBLICATIONS

U.S. Appl. No. 18/640,163, filed Apr. 19, 2024, Alexander Hee-Hanson.

U.S. Appl. No. 18/640,292, filed Apr. 19, 2024, Alexander Hee-Hanson.

U.S. Appl. No. 18/640,427, filed Apr. 19, 2024, Alexander Hee-Hanson.

U.S. Appl. No. 18/640,600, filed Apr. 19, 2024, Alexander Hee-Hanson.

International Search Report and Written Opinion in International Appln. No. PCT/US2025/024523, mailed on Jun. 10, 2025, 15 pages.

International Search Report and Written Opinion in International Appln. No. PCT/US2025/024493, mailed on Jun. 13, 2025, 19 pages.

International Search Report and Written Opinion in International Appln. No. PCT/US2025/024504, mailed on Jun. 26, 2025, 18 pages.

* cited by examiner

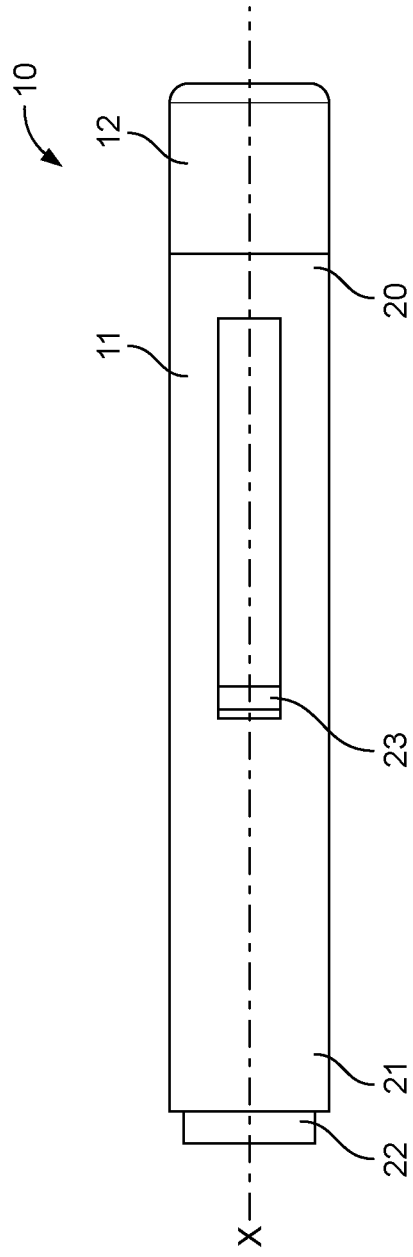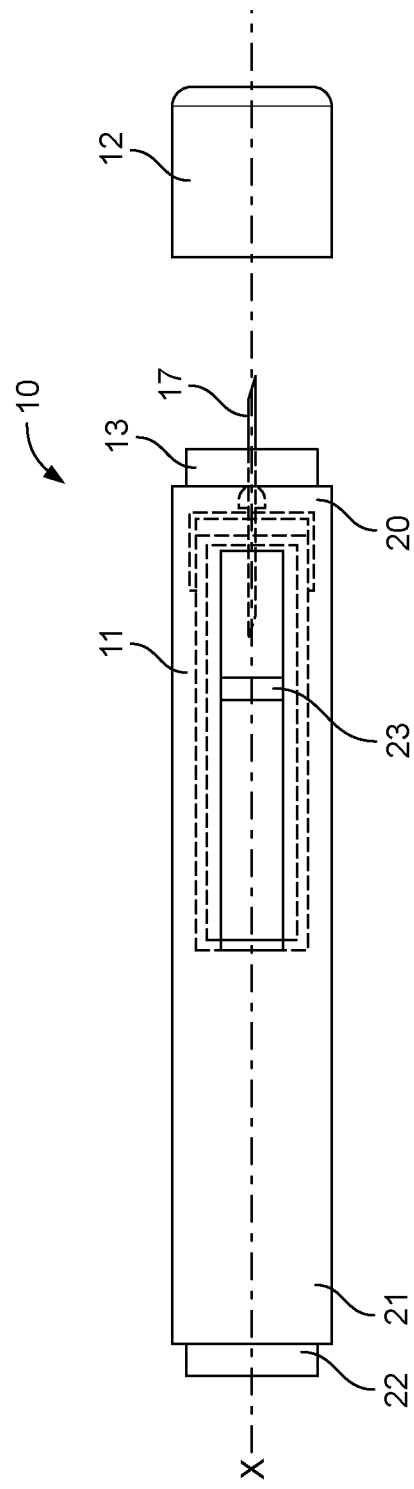
FIG. 1A
FIG. 1B

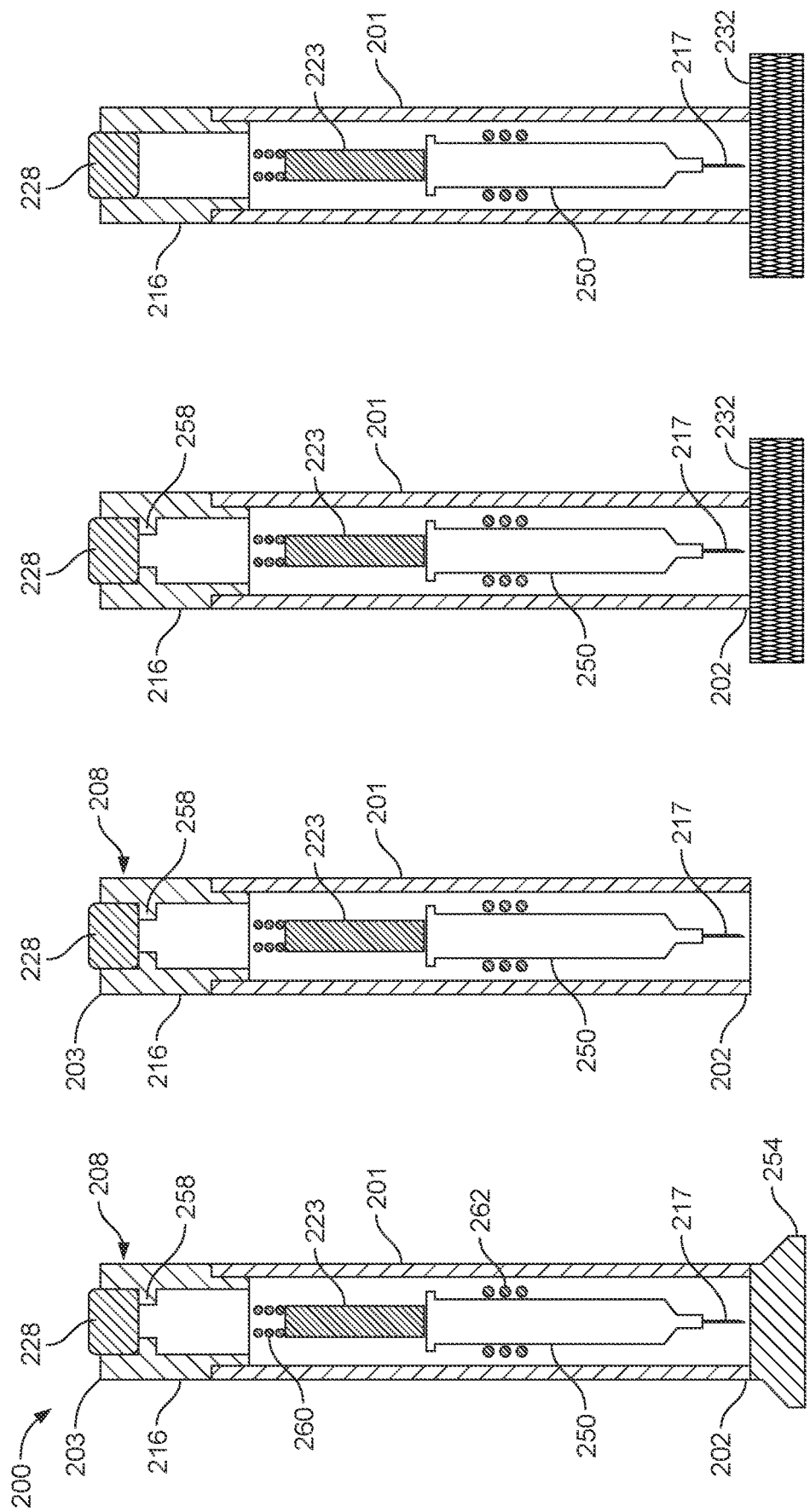

MEDICAMENT DELIVERY DEVICE

TECHNICAL FIELD

The present disclosure relates to a medicament delivery device and to a method of using a medicament delivery device.

BACKGROUND

Medicament delivery devices, such as auto-injectors, dispense medicament to an injection site of a patient. In some cases, a needle actuator is able to be depressed irrespective of whether the device has been placed at an injection site. Depressing the needle actuator independently of the device being placed at an injection site can cause the needle to be unintentionally exposed for stick injuries and can cause a dose of medicament to be unintentionally dispensed. This can lead to a waste of medicament.

SUMMARY

According to a first aspect, a medicament delivery device includes a body having a proximal end and a distal end; a needle for injecting medicament into a user, the needle is movable relative to the body from a pre-use position to an injecting position, in the pre-use position the distal end of the needle is located within the body, and in the injecting position the distal end of the needle protrudes outside of the distal end of the body for injecting medicament into a user; an actuation member which is moveable proximally relative to the body from an initial position to a protruded position, in the protruded position the proximal end of the actuation member protrudes from the proximal end of the body, and the actuation member is movable distally relatively to the body from the protruded position to an actuation position for causing the needle to move from the pre-use position to the injecting position; and a transfer member for moving the actuation member from the initial position to the protruded position, the transfer member is movable relative to the body between an extended position and a retracted position, in the extended position the distal end of the transfer member protrudes from the distal end of the body, and the retracted position is located proximally from the extended position, and one of the actuation member and the transfer member comprises a protrusion and the other of the actuation member and the transfer member comprises a drive slot, the protrusion is located in the drive slot for constraining movement of the transfer member relative to the actuation member, the drive slot comprises a circumferentially-extending portion comprising an abutment surface and the protrusion engages the abutment surface when the transfer member moves from the extended position towards the retracted position to move the actuation member from the initial position to the protruded position.

In some embodiments, the drive slot comprises an axially-extending portion for allowing the actuation member to move axially relative to the transfer member when the protrusion is located in the axially-extended portion and when the actuation member moves from the protruded position to the actuation position.

In some embodiments, the circumferentially-extending portion is orthogonal or substantially orthogonal to a longitudinal axis of the body.

In some embodiments, the actuation member is rotatable by a user relative to the body when the actuation member is in the protruded position to move the protrusion from the circumferentially-extending portion of the drive slot to the axially-extending portion of the drive slot.

In some embodiments, the circumferentially-extending portion of the drive slot has an axially-extending component of direction for translating axial movement of the protrusion into rotation of the actuation member relative to the body.

In some embodiments, the transfer member comprises a sleeve. In some cases, the transfer member is rotationally-fixed relative to the body.

In some embodiments, the device comprises a mechanism for automatically moving the needle from the pre-use position to the injecting position. In some cases, the mechanism is activated by moving the actuation member from the protruded position to the actuation position.

In some embodiments, The actuation member comprises a firing boss for engaging a part of the mechanism to activate the mechanism. In some cases, the firing boss comprises one or more protrusions for engaging the part of the mechanism to activate the mechanism. In some cases, rotation of the actuation member relative to the body moves the one or more protrusions from a first position in which the one or more protrusions are not axially aligned with the part of the mechanism to a second position in which the one or more protrusions are axially aligned with the part of the mechanism.

In some embodiments, the mechanism for automatically moving the needle from the pre-use position to the injecting position comprises a spring and a plunger which is biased distally by the spring. In some cases, when the actuation member is in the actuation position the spring is released to move the plunger distally from a proximal position to a distal position, thereby causing the needle to move from the pre-use position to the injecting position.

In some embodiments, the plunger comprises proximally-extending flexible clips, and the part of the mechanism which is engageable by the firing boss comprises the proximally-extending flexible clips.

In some embodiments, the medicament delivery device comprises an inner body which contains at least part of the mechanism for automatically moving the needle from the pre-use position to the injecting position.

In some embodiments, the proximally-extending flexible clips protrudes through an opening in the proximal end of the inner body. In some cases, the proximally-extending flexible clips engages with the inner body for maintaining the plunger in the proximal position.

In some embodiments, the one or more protrusions of the firing boss engages with the proximally-extending flexible clips. In some cases, the one or more protrusions deflect the proximally-extending flexible clips radially-inwardly for allowing the clips to move distally through the opening, and thereby releasing the spring.

In some embodiments, the device comprises a syringe for containing medicament, the syringe comprises the needle, and the plunger is connected to the syringe for moving the syringe distally. In some cases, the plunger is configured to move distally within the syringe for dispensing medicament via the needle.

In some embodiments, the mechanism for automatically moving the needle from the pre-use position to the injecting position is configured to not be activated by moving the transfer member from the extended position to the retracted position.

In some embodiments, one of the actuation member and the body comprises a guide slot, and the other of the actuation member and the body comprises a guide protrusion, the guide protrusion is located in the guide slot for constraining movement of the actuation member relative to the body.

In some embodiments, one of the actuation member and a component which is fixed relative to the body comprises a guide slot, and the other of the actuation member and the component which is fixed relative to the body comprises a guide protrusion, the guide protrusion is located in the guide slot for constraining movement of the actuation member relative to the body.

In some embodiments, the guide slot comprises an axially-extending portion, and when the protrusion engages the abutment surface, the guide protrusion is located in the axially-extending portion for allowing the actuation member to move axially relative to the body when the transfer member moves from the extended position towards the retracted position.

In some embodiments, the guide slot comprises a circumferentially-extending portion for permitting rotation of the actuation member relative to the body. In some cases, the circumferentially-extending portion of the guide slot has a first end connected to the axially-extending portion of the guide slot, when the transfer member moves from the extended position towards the retracted position, the guide protrusion travels from the axially-extending portion of the guide slot to the circumferentially extending portion of the guide slot.

In some embodiments, the axially-extending portion of the guide slot is a first axially-extending portion, and the guide slot further comprises a second axially-extending portion connected to a second end of the circumferentially extending portion of the guide slot for allowing the actuation member to move axially relative to the body when the actuation member moves from the protruded position to the actuation position.

In some embodiments, the guide slot comprises a diagonally-extending portion connecting the second axially-extending portion to the first axially-extending portion for allowing the guide protrusion to return to the first axially-extending portion of the guide slot and the transfer member to return to the extended position.

In some embodiments, the device further comprises a biasing means for biasing the transfer member in a direction from the retracted position towards the extended position. In some cases, the biasing means comprises a spring.

In some embodiments, the device further comprises a cap which is removably attachable to the body, the cap covers the distal end of the transfer member for preventing the transfer member being moved from the extended position to the retracted position when the cap is attached to the body.

In some embodiments, the medicament delivery device further comprises a lock ring which is rotatable from a pre-use position, in which the lock ring prevents movement of the actuation member from the protruded position towards the actuation position, to a use position in which the lock ring permits movement of the actuation member from the protruded position towards the actuation position.

In some embodiments, the actuation member comprises a button for pressing by a user for moving the actuation member from the protruded position to the actuation position.

In some embodiments, when the actuation member is in the initial position, the proximal end of the button is flush with the proximal end of the body or the proximal end of the button is located distally from the proximal end of the body.

In some embodiments, the actuation member is in the form of a button.

In some embodiments, the device comprises a container for containing medicament. In some cases, the container is a syringe which comprises the needle.

In some embodiments, the container contains the medicament.

According to another aspect, a method of using a medicament delivery device includes moving a distal end of a transfer member proximally relative to a body from an extended position to a retracted position, in the extended position, the distal end of the transfer member protrudes distally from the distal end of the body, movement of the transfer member from the extended position to the retracted position moves an actuation member proximally relative to the body from an initial position to a protruded position, the actuation member is movable distally relative to the body from the protruded position to an actuation position for causing a needle to move from a pre-use position, in which a distal end of a needle is located within the body, to an injecting position in which the distal end of the needle protrudes outside of the distal end of the body for injecting medicament into a user.

In some embodiments, the method comprises rotating the actuation member relative to the body.

In some embodiments, rotating the actuation member relative to the body comprises rotating the actuation member when the actuation member is in the protruded position.

In some embodiments, rotating the actuation member relative to the body comprises gripping the actuation member when the actuation member is in the protruded position and rotating the actuation member relative to the body.

In some embodiments, rotating the actuation member relative to the body comprises the transfer member rotating the actuation member when it moves from the extended position to the retracted position.

According to another aspect, a method of using a medicament delivery device includes pressing a distal end of a transfer member against an injection site to move the transfer member relative to a body from an extended position to a retracted position, movement of the transfer member from the extended position to the retracted position moves an actuation member relative to the body from an initial position to a protruded position, and moving the actuation member distally relative to the body from the protruded position to an actuation position.

In some embodiments, moving the actuation member distally relative to the body from the protruded position to the actuation position causes a needle to move from a pre-use position, in which a distal end of a needle is located within the body, to an injecting position in which the distal end of the needle protrudes outside of the distal end of the body for injecting medicament into a user.

In some embodiments, the device comprises a mechanism for automatically moving the needle from the pre-use position to the injecting position. In some cases, moving the actuation member distally relative to the body from the protruded position to the actuation position activates the mechanism.

In some embodiments, the actuation member comprises a firing boss for engaging a part of the mechanism to activate the mechanism. In some cases, the firing boss comprises one or more protrusions. In some cases, the method comprises rotating the actuation member relative to the body to move the one or more protrusions from a first position in which the one or more protrusions are not axially aligned with the part of the mechanism to a second position in which the one or more protrusions are axially aligned with the part of the mechanism for engaging the part of the mechanism when the actuation member is moved to the actuation position.

In some embodiments, the method further comprises rotating a lock ring from a pre-use position, in which the lock ring prevents movement of the actuation member from the protruded position towards the actuation position, to a use position in which the lock ring permits movement of the actuation member from the protruded position towards the actuation position.

In some embodiments, the method further comprises rotating the lock ring prior to pressing the distal end of the transfer member against the injection site.

In some embodiments, the method further comprises removing a cap from the medicament delivery device.

In some embodiments, the methods described herein comprises using a medicament delivery device having any of the features described herein.

In an aspect, a medicament delivery device includes:
a body having a proximal end and a distal end;
a needle configured to be movable relative to the body from a pre-use position in which a distal end of the needle is located proximal to the distal end of the body to (ii) an injection position in which the distal end of the needle is distal to the distal end of the body for injecting a medicament;
an actuation member configured to be movable proximally relative to the body from (i) an initial position to (ii) a protruded position in which a proximal end of the actuation member protrudes from a proximal end of the body to (iii) an actuation position, the medicament delivery device being configured such that moving the actuation member distally relatively to the body from the protruded position to the actuation position moves the needle from the pre-use position to the injection position; and
a transfer member configured to move the actuation member from the initial position to the protruded position, the transfer member being movable relative to the body between (i) an extended position in which a distal end of the transfer member protrudes from the distal end of the body and (ii) a retracted position in which the transfer member is located proximally from the extended position,
wherein one of the actuation member or the transfer member comprises a protrusion and the other of the actuation member or the transfer member comprises a drive slot, the protrusion configured to be located in the drive slot for limiting movement of the transfer member relative to the actuation member, the drive slot comprising a circumferentially-extending portion comprising an abutment surface, and the medicament delivery device being configured such that the protrusion engages the abutment surface when the transfer member moves from the extended position towards the retracted position to move the actuation member from the initial position to the protruded position.

In some embodiments, the drive slot comprises an axially-extending portion for allowing the actuation member to move axially relative to the transfer member when the protrusion is located in the axially-extended portion and when the actuation member moves from the protruded position to the actuation position.

In some embodiments, the actuation member is rotatable by a user relative to the body when the actuation member is in the protruded position to move the protrusion from the circumferentially-extending portion of the drive slot to the axially-extending portion of the drive slot.

In some embodiments, the circumferentially-extending portion is orthogonal or substantially orthogonal to a longitudinal axis of the body.

In some embodiments, the medicament delivery device includes a mechanism for automatically moving the needle from the pre-use position to the injection position, the mechanism configured to be activated by moving the actuation member from the protruded position to the actuation position.

In some embodiments, the actuation member comprises a boss for engaging a part of the mechanism to activate the mechanism. In some cases, the boss is a firing boss.

In some embodiments, the boss comprises one or more protrusions for engaging the part of the mechanism to activate the mechanism, wherein the medicament delivery device is configured such that rotation of the actuation member relative to the body moves the one or more protrusions from a first position in which the one or more protrusions are not axially aligned with the part of the mechanism to a second position in which the one or more protrusions are axially aligned with the part of the mechanism.

In some embodiments, the medicament delivery device is configured such that the mechanism is not activated by moving the transfer member from the extended position to the retracted position.

In some embodiments, the circumferentially-extending portion of the drive slot has an axially-extending component of direction for translating axial movement of the protrusion into rotation of the actuation member relative to the body.

In some embodiments, one of the actuation member or the body or a component which is fixed relative to the body comprises a guide slot, and the other of the actuation member or the body or the component which is fixed relative to the body comprises a guide protrusion, the guide protrusion being located in the guide slot for limiting movement of the actuation member relative to the body.

In some embodiments, the guide slot comprises a circumferentially-extending portion for permitting rotation of the actuation member relative to the body.

In some embodiments, the guide slot comprises an axially-extending portion, and the medicament delivery device is configured such that when the protrusion engages the abutment surface, the guide protrusion is located in the axially-extending portion for allowing the actuation member to move axially relative to the body when the transfer member moves from the extended position towards the retracted position.

In some embodiments, the guide slot comprises a circumferentially-extending portion for allowing rotation of the actuation member relative to the body, the circumferentially-extending portion of the guide slot having a first end connected to the axially-extending portion of the guide slot, and the medicament delivery device configured such that when the transfer member moves from the extended position towards the retracted position, the guide protrusion travels from the axially-extending portion of the guide slot to the circumferentially extending portion of the guide slot.

In some embodiments, the axially-extending portion of the guide slot is a first axially-extending portion, and the guide slot further comprises a second axially-extending portion connected to a second end of the circumferentially extending portion of the guide slot for allowing the actuation member to move axially relative to the body when the actuation member moves from the protruded position to the actuation position.

In some embodiments, the guide slot comprises a diagonally-extending portion connecting the second axially-extending portion to the first axially-extending portion for allowing the guide protrusion to return to the first axially-extending portion of the guide slot and the transfer member to return to the extended position.

In some embodiments, the medicament delivery device includes a biasing member for biasing the transfer member in a direction from the retracted position towards the extended position. In some cases, the biasing member comprises or is a spring.

In some embodiments, the medicament delivery device includes a cap configured to be removably attachable to the body, the cap configured to cover the distal end of the transfer member for limiting the transfer member being moved from the extended position to the retracted position when the cap is attached to the body.

In some embodiments, the medicament delivery device includes a lock ring configured to be rotatable from (i) a first lock ring position in which the lock ring limits movement of the actuation member from the protruded position towards the actuation position to (ii) a second lock ring position in which the lock ring allows movement of the actuation member from the protruded position towards the actuation position.

In some embodiments, the actuation member comprises a button configured to be pressed by a user to move the actuation member from the protruded position to the actuation position.

In some embodiments, the medicament delivery device is configured such that when the actuation member is in the initial position, the proximal end of the button is substantially flush with the proximal end of the body.

In some embodiments, the medicament delivery device is configured such that when the actuation member is in the initial position, a proximal end of the button is located distally from the proximal end of the body.

In some embodiments, the device comprises a container for containing medicament. In some cases, the container is a syringe comprising the needle. In some cases, the container contains the medicament.

In an aspect, a medicament delivery device includes:
a body;
a first member configured to be axially and rotationally movable relative to the body, the first member comprising a first slot having an axial portion and a circumferential portion; and
a second member configured to be axially movable relative to the body, the second member comprising a first protrusion configured to engage the first slot of the first member,
wherein the medicament delivery device is configured to have (i) a first state in which the protrusion is located in the circumferential portion of the first slot to axially couple the first member to the second member such that proximal movement of the second member relative to the body causes a proximal movement of the first member relative to the body and (ii) a second state in which the protrusion is located in the axial portion of the first slot to axially decouple the first member and the second member such that distal movement of the first member relative to the second member is allowed.

In an aspect, a method includes:
moving a distal end of a transfer member of a medicament delivery device proximally relative to a body of the medicament delivery device from (i) an extended position in which the distal end of the transfer member protrudes distally from a distal end of the body to (ii) a retracted position such that movement of the transfer member from the extended position to the retracted position moves an actuation member of the medicament delivery device proximally relative to the body from (i) an initial position to a (ii) protruded position, wherein the actuation member is movable distally relative to the body from the protruded position to an actuation position for moving a needle from (i) a pre-use position in which a distal end of the needle is proximal to the distal end of the body to (ii) an injection position in which the distal end of the needle is proximal to the distal end of the body.

In some embodiments, the method includes rotating the actuation member relative to the body.

In some embodiments, rotating the actuation member relative to the body comprises rotating the actuation member when the actuation member is in the protruded position.

In some embodiments, rotating the actuation member relative to the body comprises the transfer member rotating the actuation member when the transfer member moves from the extended position to the retracted position.

In an aspect, a method includes:
pressing a distal end of a transfer member of a medicament delivery device against an injection site to move the transfer member relative to a body of the medicament delivery device from an extended position to a retracted position to move an actuation member of the medicament delivery device relative to the body from an initial position to a protruded position; and
moving the actuation member distally relative to the body from the protruded position to an actuation position.

In some embodiments, the method includes rotating a lock ring from (i) a first lock ring position in which the lock ring limits movement of the actuation member from the protruded position towards the actuation position to (ii) a second lock ring position in which the lock ring allows movement of the actuation member from the protruded position towards the actuation position.

In some embodiments, the method includes removing a cap from the medicament delivery device.

BRIEF DESCRIPTION OF THE DRAWINGS

Embodiments will now be described, by way of example only, with reference to the accompanying drawings, in which:

FIG. 1A is a schematic view of a medicament delivery device with a cap attached;

FIG. 1B is a schematic view of the medicament delivery device of FIG. 1A with the cap removed;

FIG. 2A is a schematic view of a medicament delivery device prior to use (i.e. in a pre-use configuration);

FIG. 2B is a schematic view of the device of FIG. 2A with the cap removed;

FIG. 2C is a schematic view of the device of FIG. 2A showing the device placed at an injection site;

FIG. 2D is a schematic view of the device of FIG. 2A with a lock ring of the device having been rotated to allow a button of the device to be depressed by a user;

DETAILED DESCRIPTION

Figure 2G:
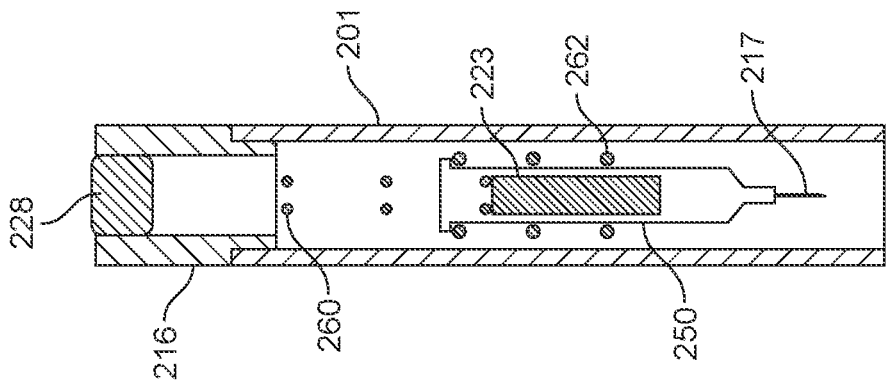
FIG. 2G is a schematic view of the device of FIG. 2A showing the device removed from the injection site after the needle has retracted within the device after delivery of the dose.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe to a more distal location within the syringe in order to force a medicament from the syringe through needle 17. In some embodiments, a drive spring is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring, located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

FIGS. 2A to 2G show the sequential steps of operating a medicament injection device 400.

As shown in FIG. 2A, the device 200 comprises a body 201, a syringe having a needle 217 and an axially movable plunger 223 for dispensing medicament from the syringe 250. The device comprises a cap 254 which is removably attached to the body 201 and covers a distal end 202 of the body 201 so as to prevent stick injuries.

As shown in FIGS. 2B-2C, in order to deliver a dose of medicament to an injection site, the cap 254 is removed (FIG. 2B) and the device is placed at an injection site 232 (FIG. 2C). A needle actuator in the form of a button 228, is prevented from being depressed by a locking member 208 in the form of a lock ring 216 which is rotatable by a user about a longitudinal axis of the device, by a radially projecting stop 258 provided in the locking member 208. In FIG. 2D, in order to allow the button 228 to be depressed by a user, the lock ring 216 is rotated about the longitudinal axis of the device to a needle actuator release position (or button release position) in which the stop 258 no longer prevents the button 228 from being depressed by a user.

Figure 2F:
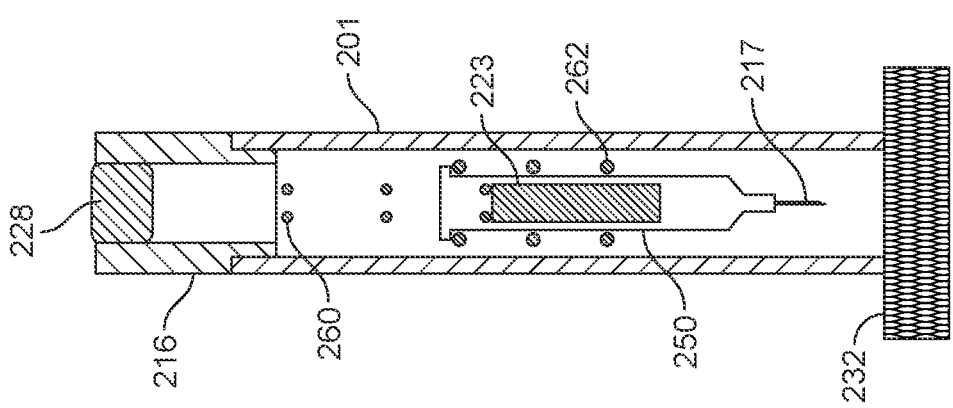
FIG. 2F is a schematic view of the device of FIG. 2A showing the needle having retracted within the device after a dose has been delivered.
Figure 2E:
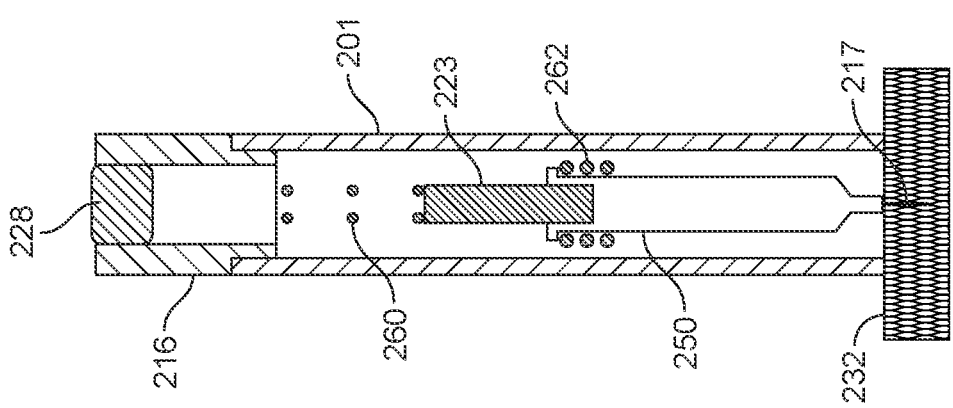
FIG. 2E is a schematic view of the device of FIG. 2A after the button has been depressed and the needle has been caused to move to an exposed position.

Turning now to FIG. 2E, the user then depresses the button 228 to actuate or trigger a needle mechanism so as to release the syringe 250 for distal axial movement towards the injection site 232 such that the needle 217 moves from a pre-use retracted position to an exposed (or "uncovered") position for delivering medicament to the injection site 232 under a biasing force provided by a bias in the form of a compression spring 260. Depressing the button 228 also releases the plunger 223 which, biased by the bias 260, moves along the syringe 250 towards the distal end 204 of the device 200 to force medicament within the syringe 250 through the needle 217, thereby delivering a dose of medicament. As shown in FIG. 2F, once the dose has been delivered, a medicament container bias 262, embodied by a further spring 262, then causes the needle 202 to move axially back to the retracted position, away from the injection site 232 in a proximal direction. As shown in FIG. 2G, the device 200 is then removed from the injection site 232, for later reuse or for disposal.

Figure 3A:
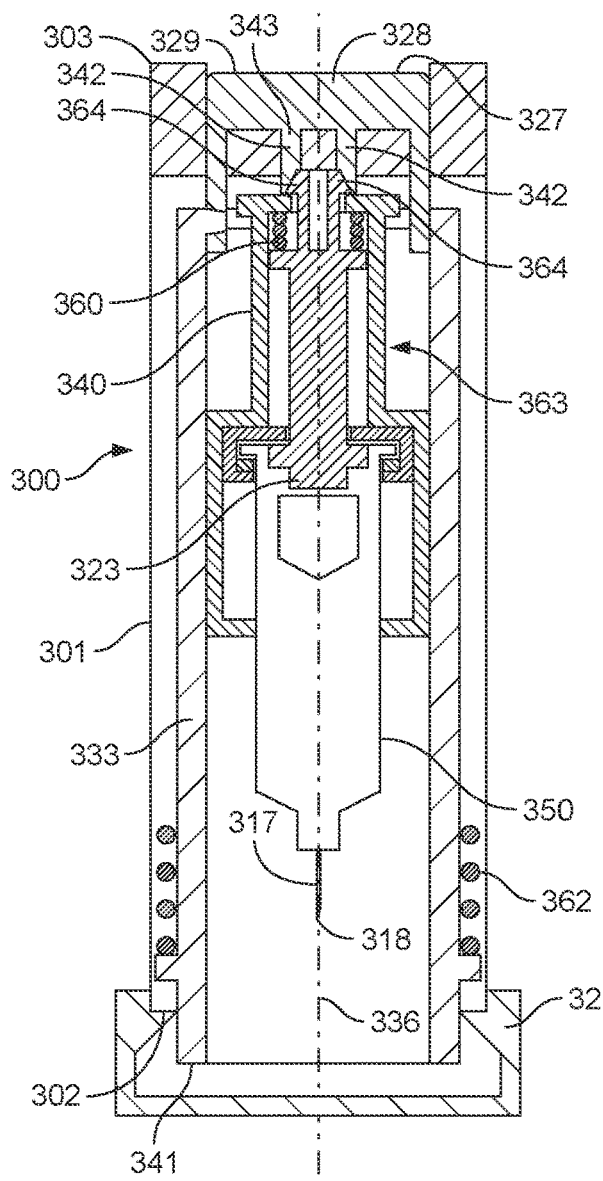
FIG. 3A is a schematic view of a medicament delivery device.

FIG. 3A is a schematic view of parts of a medicament delivery device 300.

Figure 3B:
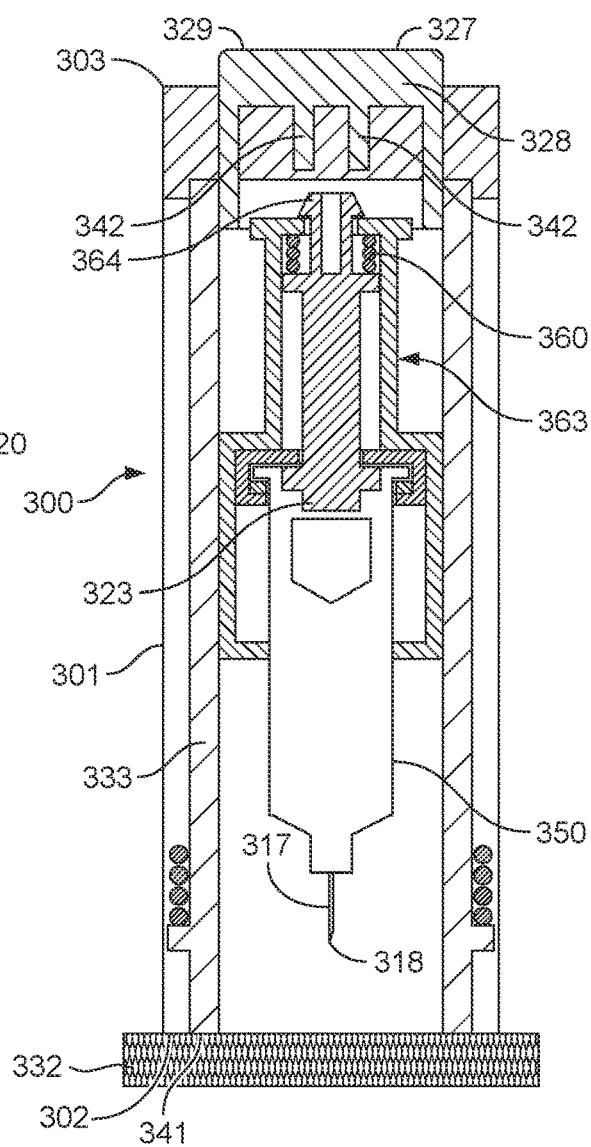
FIG. 3B is a schematic view of the device of FIG. 3A on an injection site, with the transfer member in the retracted position and the actuation member is in the protruded position.
Figure 3C:
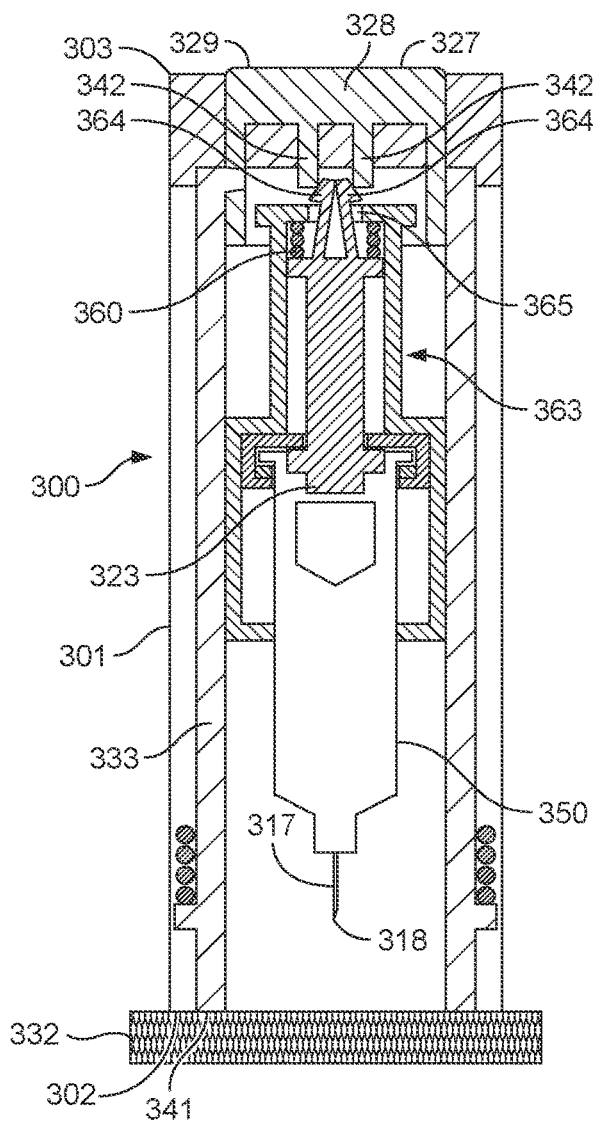
FIG. 3C is a schematic view of the device of FIG. 3A with the actuation member moving towards the actuation position.
Figure 3D:
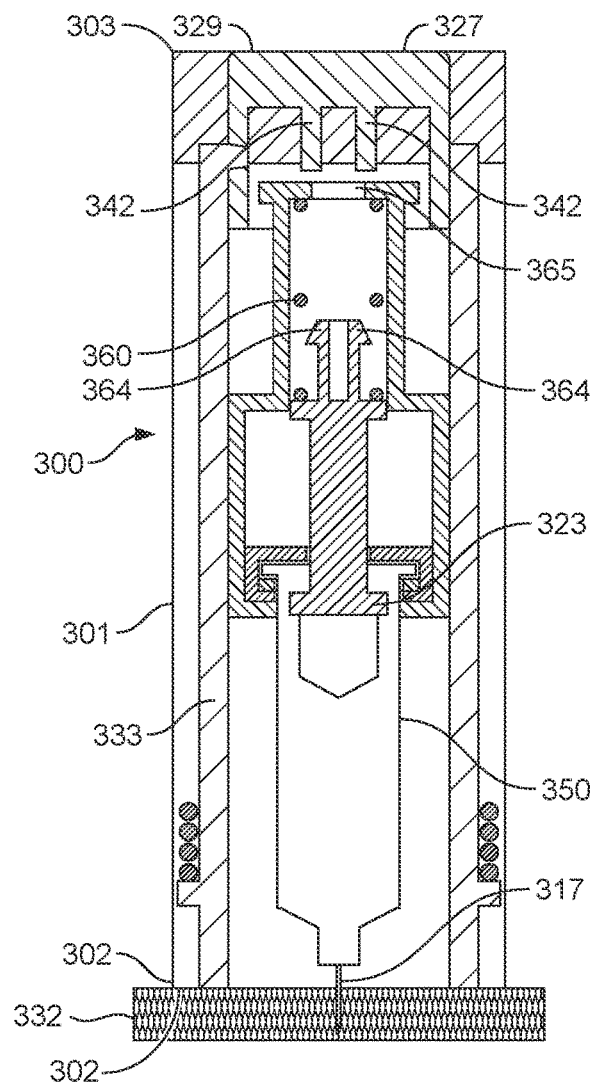
FIG. 3D is a schematic view of the device of FIG. 3A with the needle in the injecting position.

The medicament delivery device 300 has a body 301 having a proximal end 303 and a distal end 302. The device has a needle 317 for injecting medicament into a user. The needle 317 is movable relative to the body 301 from a pre-use position to an injecting position. In the pre-use position the distal end of the needle 318 is located within the body 301, and in the injecting position the distal end of the needle 318 protrudes outside of the distal end of the body 301 for injecting medicament into a user. FIG. 3A shows an example of the needle 317 in the pre-use position, and FIG. 3D shows an example of the needle 317 in the injecting position.

The needle 317 is part of a syringe 350 which contains medicament. In some embodiments, a container such as a cartridge of medicament is included which is initially separated from the needle.

The medicament delivery device 300 comprises an actuation member 327. The actuation member 327 is movable proximally relative to the body 301 from an initial position to a protruded position. In the protruded position the proximal end of the actuation member protrudes from the proximal end of the body 303. The actuation member 327 comprises a button for pressing by a user for moving the actuation member 327 from the protruded position to an actuation position. When the actuation member 327 is in the initial position, the proximal end 329 of the button 328 is located distally from the proximal end of the body 303. Alternatively, when the actuation member 327 is in the initial position the proximal end 329 of the button 328 is flush with the proximal end of the body 303 or the proximal end 329 of the button 328 is proximal of the proximal end of the body 303. FIG. 3A shows an example of the actuation member 327 in the initial position. FIG. 3B shows an example of the actuation member 327 in the protruded position. The protruded position is located proximally from the first position.

The actuation member 327 is movable distally relative to the body 301 from the protruded position to an actuation position for causing the needle to move from the pre-use position to the injecting position. FIG. 3C shows an example of the actuation member 327 in the actuation position. The actuation position is located distally from the protruded position.

The device 300 comprises a transfer member 333 for moving the actuation member 327 from the initial position to the protruded position. The transfer member 333 is located within the body 301. The transfer member 333 is movable proximally relative to the body 301 between an extended position and a retracted position. In the extended position the distal end of the transfer member 341 protrudes from the distal end of the body 302 as shown, for example, in FIG. 3A. FIG. 3B shows an example of the transfer member 333 in the retracted position, in which the distal end 341 of the transfer member 333 is flush with the distal end of the body 302. The transfer member 333 is in the retracted position in FIGS. 3C and 3D. In some embodiments, the distal end 341 of the transfer member 333 may be located distally from the distal end 302 of the body when the transfer member is in the retracted position. The retracted position is located proximally from the extended position.

The medicament delivery device 300 has a biasing means in the form of a spring 362 for biasing the transfer member 333 towards the extended position. The spring 362 allows the transfer member 333 to return to the extended position if the transfer member 333 is removed from the injection site. In some embodiments, the spring 362 may be omitted, for example to reduce the cost or mass of the device, or the force required to move the transfer member 333. The transfer member 333 comprises a sleeve. The sleeve is located within the body 301. In some embodiments, the transfer member 333 can comprise an axially-extending member which is not in the form of the sleeve. The sleeve is co-axial or substantially co-axial with the longitudinal axis of the body 336. The sleeve may be rotationally-fixed relative to the body.

The actuation member 327 is movable relative to the body from the protruded position to an actuation position for causing the needle to move from the pre-use position to the injecting position. FIG. 3C shows an example of the actuation member 327 in the actuation position. When the actuation member 327 is in the actuation position, the needle 317 is caused to move to its injecting position. This can be by the actuation member 327 exerting a force which moves the needle 317 directly to the injecting position or the actuation member 327 can activate a mechanism 363 which automatically causes the needle 317 to move to the injecting position when the actuation member 327 is in the actuation position.

The example device 300 comprises a mechanism 363 for automatically moving the needle from the pre-use position to the injecting position. The mechanism 363 comprises a plunger 323 and a spring 360. The plunger 323 is biased distally by the spring 360. The mechanism 363 is at least partially housed within an inner body 340. The inner body 340 is housed within the body 301. The plunger 323 comprises proximally-extending clips 364. The spring 360 is retained in the compressed position by virtue of the clips 364 which protrude through a proximal opening 365 in the inner body 340. The clips 364 engage with the inner body 340 for maintaining the plunger 323 in a proximal position. Alternatively, the clips 364 could engage with another component of the device.

The mechanism 363 is activated by the user moving the actuation member 327 from the protruded position to the actuation position. When the actuation member 327 is in the actuation position, the spring 360 is released to move the plunger distally to thereby move the syringe 350 distally, and to dispense the medicament from the syringe 350 via the needle 317 as the plunger 323 moves distally within the syringe 350. The actuation member 327 has a firing boss for engaging a part of the mechanism to activate the mechanism. The firing boss comprises one or more protrusions 342 which engage with the clips 364 to flex the clips radially inwardly for allowing the clips to move distally through the proximal opening 365, thereby releasing the spring 360.

Some embodiments use a different mechanism. In some embodiments, movement of the actuation member 327 from the protruded position to the actuation position causes (e.g., only causes) the needle 317 to move from the pre-use position to the injecting position. In some embodiments, the movement of the actuation member 327 from the first position to the second position causes additional steps to be performed, such as the automatic dispensing of the medicament from the device via the needle.

In some embodiments, the movement of the transfer member 333 from the extended position to the retracted position does not activate the mechanism 363 for automatically moving the needle from the pre-use position to the injecting position.

The medicament delivery device 300 may additionally comprise a lock ring 216, as shown and described in relation to FIGS. 2A to 2G above. The lock ring is rotatable from a pre-use position, in which the lock ring prevents movement of the actuation member from the first position towards the second position, to a use position in which the lock ring permits movement of the actuation member from the first position towards the second position.

The medicament delivery device 300 additionally has a cap 320. The cap 320 is removably attached to the body 301 and covers the distal end of the transfer member 341 for preventing the transfer member 300 from being moved from the extended position to the retracted position when the cap 320 is attached to the body 301. The cap 320 prevents the device being accidentally activated prior to the cap 320 being removed from the body 301 since the actuation member 327 cannot be accidentally moved to the protruded position. The cap 320 may be attached to the body 301, for example, by a screw-threaded or a press fit connection. The cap 320 is optional and in some embodiments, the device may not have a cap.

As noted, the device 300 comprises a transfer member 333 for moving the actuation member 327 from the initial position to the protruded position. This allows the button to be presented to a user when the transfer member 333 has been pushed against the injection site 332. The proximal end 329 of the button 328 may be located distally from or flush with the proximal end of the body 303 when the actuation member is in the initial position so that the actuation member is fully housed within the body 301 for preventing accidental activation of the device through pressing the activation member 327 prior to the device being pressed against the injection site.

Alternatively the proximal end of the button 329 may be located proximally of the proximal end of the housing 303 when the actuation member 327 is in the initial position. The protruded position is located proximally form the initial position. A user may recognize the difference between the initial position and the protruded position and know to activate the device only when the actuation member 327 is in the protruded position.

In order for the transfer member 333 to move the actuation member 327 from the initial position to the protruded position, a drive slot and a protrusion may provided. For example, the actuation member 327 comprises a drive slot and the transfer member 333 comprises a protrusion which is located in the drive slot, or the transfer member 333 comprises a drive slot and the actuation member 327 comprises a protrusion which is located in the drive slot. FIGS. 4A to 4D and 5A to 5E illustrate examples of a drive slot and protrusion which can be used in the device 300 of FIGS. 3A to 3D, or in other medicament delivery devices such as those described or contemplated herein.

Figure 4A:
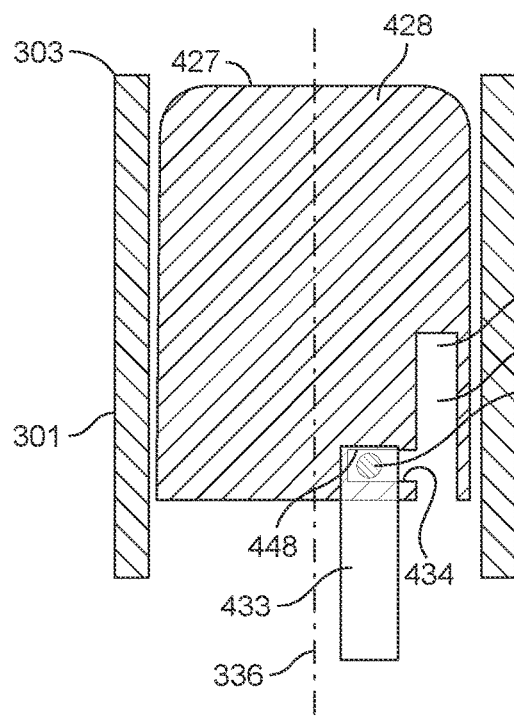
FIG. 4A is a schematic view of parts of a medicament delivery device.
Figure 4B:
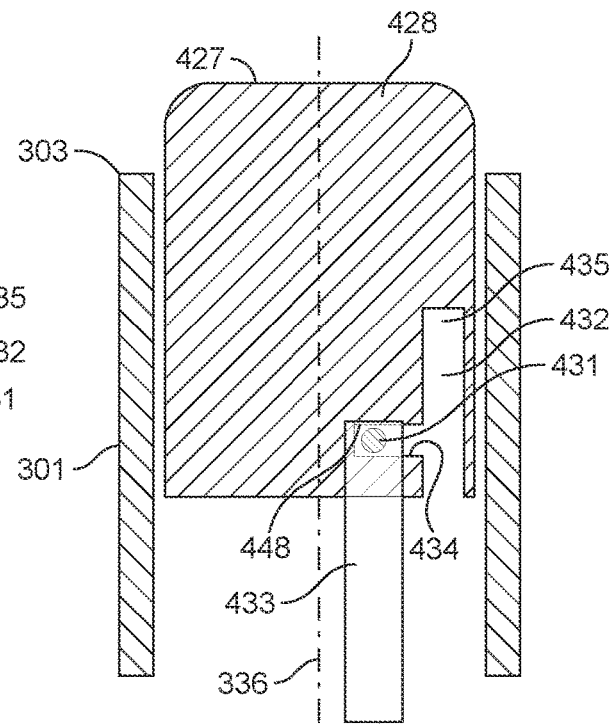
FIG. 4B is a schematic view of the device of FIG. 4A with the actuation member in the protruded position.

FIGS. 4A to 4D show schematic views of part of a medicament delivery device. In FIGS. 4A to 4D, the actuation member 427 comprises a drive slot 432. The transfer member 433 comprises a protrusion 431. The protrusion 431 is located in the drive slot 432 for constraining movement of the transfer member 433 relative to the actuation member 427. The drive slot 432 comprises a circumferentially-extending portion 434 comprising an abutment surface 448. The abutment surface 448 is formed by part of the surface of the drive slot in the circumferentially-extending portion 434. The protrusion 431 engages the abutment surface 448 when the transfer member 433 moves from the extended position towards the retracted position to move the actuation member 427 from the initial position to the protruded position. FIG. 4A shows an example of the actuation member 427 in the initial position. FIG. 4B shows an example of the actuation member in the protruded position. In some examples, the circumferentially-extending portion 434 extends at least partially around a circumference of the activation member 427. For example, the circumferentially-extending portion 434 extends circumferentially on the activation member 427.

The circumferentially-extending portion 434 of the drive slot is orthogonal or substantially orthogonal to the longitudinal axis 336 of the body.

Figure 4C:
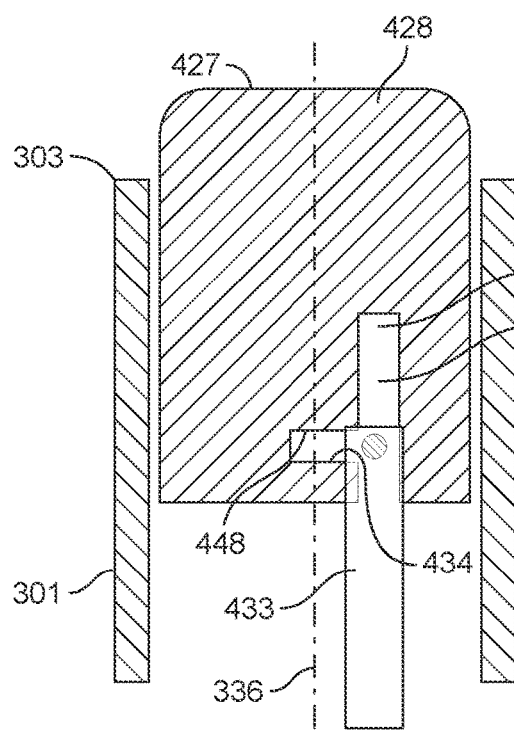
FIG. 4C is a schematic view of the device of FIG. 4A with the actuation member rotated relative to the body.
Figure 4D:
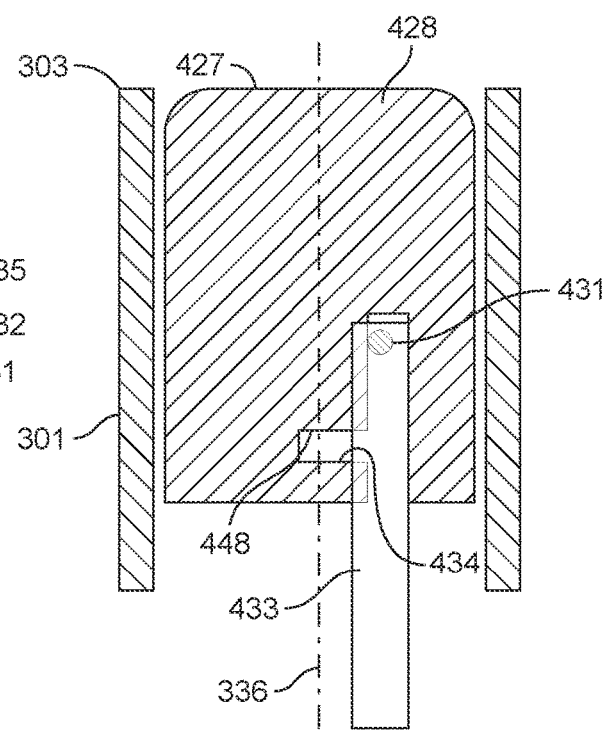
FIG. 4D is a schematic view of the device of FIG. 4A with the actuation member in the actuation position.

The drive slot 432 has an axially-extending portion 435 connected to the circumferentially-extending portion 434. When the actuation member 427 is in the protruded position, the actuation member can be gripped by a user and rotated by the user relative to the body 301 to move the protrusion 431 from the circumferentially-extending portion 434 of the drive slot to the axially-extending portion 435 of the drive slot. Alternatively, instead of a user gripping the actuation member to rotate it relative to the body, the actuation member may be rotated relative to the body in another way, such as by a user rotating a lock ring which is rotationally connected to the actuation member. FIG. 4C shows an example of the actuation member 427 after it has been rotated relative to the body. The axially-extending portion 435 of the drive slot is parallel to or substantially parallel to the longitudinal axis of the body 336.

When the protrusion 431 is located in the axially-extended portion 435 of the drive slot, the actuation member 427 can move axially relative to the transfer member 433. The actuation member 427 can be moved from the protruded position to the actuation position as shown, for example in FIG. 4D. The protrusion 431 travels along the axially extending portion 435 of the drive slot when the actuation member 427 moves from the protruded position to the actuation position.

If a user removes the transfer member 433 from the injection site while the protrusion 431 is in the circumferentially-extending portion of the drive slot 434, and if the medicament delivery device has a biasing means such as a spring 362 for biasing the transfer member 433 towards the extended position, then the biasing means allows the transfer member 433 to return to the extended position upon removal of the device from the injection site.

The protrusion 431 is at the proximal end of the transfer member 433. In some embodiments, the protrusion may be located distally from the proximal end of the transfer member 433.

In the example of FIGS. 4A to 4D, the protrusion 431 is provided on the transfer member 433 and the drive slot 432 is provided on the actuation member 427. However, in some embodiments, the protrusion 431 is provided on the actuation member 427 and the drive slot 432 is provided on the transfer member 333.

In use, a user places the distal end of the transfer member 433 against an injection site to move the blocking member 433 from the extended position to the retracted position. The engagement of the protrusion 431 with the abutment surface 448 transfers proximal movement of the transfer member 433 into proximal movement of the actuation member 427 to move the actuation member from the initial position to the protruded position. The device presents the button to a user for activation.

When the actuation member 427 is in the protruded position, a user rotates the actuation member 427 relative to the body 301. The rotation moves the protrusion 431 from the circumferentially-extending portion of the drive slot 434 to the axially-extending portion of the drive slot 435.

A user can then move the actuation member 427 distally relative to the body 301 from the protruded position to the actuation position for causing the needle to move from the pre-use position to the injecting position. If the actuation member 427 comprises a button 428 then a user presses the button 428 towards the body 301 to move the actuation member distally relative to the body 301. When the actuation member moves from the protruded position to the actuation position then the needle is caused to move from the pre-use position to the injecting position, for example by the actuation member activating a mechanism for automatically moving the needle from the pre-use position to the injecting position, as described, for example, in relation to the medicament delivery device 300.

FIGS. 5A to 5E show schematic views of part of a medicament delivery device. In FIGS. 5A to 5E, the actuation member 527 comprises a drive slot 532. The transfer member 533 comprises a protrusion 531. The protrusion 531 is located in the drive slot 532 for constraining movement of the transfer member 533 relative to the actuation member 527.

Figure 5A:
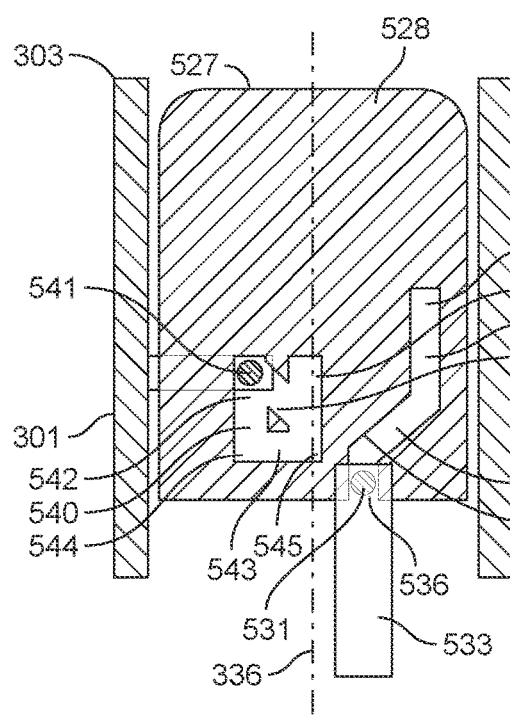
FIG. 5A is a schematic view of parts of a medicament delivery device.

The drive slot 532 comprises a circumferentially-extending portion 534 comprising an abutment surface 548. The abutment surface 548 is formed by part of the surface of the drive slot in the circumferentially-extending portion 534. The protrusion 531 engages the abutment surface 548 when the transfer member 533 moves from the extended position towards the retracted position to move the actuation member 527 from the initial position to the protruded position. FIG. 5A shows an example of the actuation member 527 in the initial position. FIG. 5C shows an example of the actuation member 527 in the protruded position.

The drive slot 532 comprises a first axially-extending portion 536 connected to the circumferentially-extending portion of the drive slot 534. The protrusion 531 is located in the first axially-extending portion 536 when the transfer member 333 is in the extended position. This allows the transfer member 533 to move proximally before it enters the circumferentially-extending portion of the drive slot 534 and the protrusion 531 engages the abutment surface. The first axially-extending portion 536 is parallel to or substantially parallel to the longitudinal axis of the body 336. In some embodiments, the drive slot does not have a first axially-extending portion 536 and the protrusion is located in the circumferentially-extending portion 534 when the transfer member 533 is in the extended position.

The circumferentially-extending portion of the drive slot 534 has an axially-extending component of direction for translating axial movement of the protrusion 531 into rotation of the actuation member 527 relative to the body 301.

The drive slot 532 has a second axially-extending portion 535 connected to the circumferentially-extending portion 534. The second axially-extending portion 535 is connected to the circumferentially-extending portion 534 at the opposite end to the first axially-extending portion 536. The second axially-extending portion 535 is parallel to or substantially parallel to the longitudinal axis of the body 336.

When the actuation member 527 is in the protruded position and has been rotated relative to the body 301, the protrusion 531 is moved to the second axially-extending portion 535 of the drive slot. FIG. 5D shows an example of the actuation member 527 after it has been rotated.

When the protrusion 531 is located in the second axially-extended portion 535 of the drive slot, the actuation member 527 can move axially relative to the transfer member 533. The actuation member 327 can be moved from the protruded position to the actuation position as shown, for example in FIG. 5E. The protrusion 531 travels along the second axially extending portion 535 of the drive slot when the actuation member 527 moves form the protruded position to the actuation position.

The actuation member 527 comprises a guide slot 540. The medicament delivery device comprises a guide protrusion 541 which is fixed relative to the body 301. The guide protrusion 541 may be provided on an inner surface of the body 301, or a surface of an internal component, for example. The guide protrusion 541 is located in the guide slot 540 for constraining movement of the actuation member 527 relative to the body 301.

Alternatively, in some embodiments, the guide protrusion 541 is provided on the actuation member 527 and the guide slot is provided on the body 301. In some embodiments, the guide slot is provided on a component which is fixed relative to the body 301 for constraining movement of the actuation member 527 relative to the body 301.

The guide slot 540 has a first axially-extending portion 542. When the protrusion 531 on the transfer member 533 engages the abutment surface 548, the guide protrusion 541 is located in the first axially-extending portion 542 of the guide slot 540 for allowing the actuation member 527 to move axially relative to the body 301 when the transfer member moves from the extended position towards the retracted position. The protrusion 541 and the first-axially extending portion 542 of the guide slot 540 constrain the rotational movement of the actuation member 527 relative to the body 301. In FIGS. 5A to 5E the first axially-extending portion 542 of the guide slot is parallel to the longitudinal axis of the body 336. In some embodiments, the first axially-extending portion 542 may have a circumferential component of direction so that the first axially-extending portion 542 is at an angle relative to the longitudinal axis of the body 336.

The guide slot 540 has a circumferentially-extending portion 543 for permitting rotation of the actuation member 527 relative to the body 301. The circumferentially-extending portion of the guide slot 543 has a first end 544 connected to the first axially-extending portion of the guide slot 542. When the transfer member 533 moves from the extended position towards the retracted position, the guide protrusion 541 travels from the first axially-extending portion of the guide slot 542 to the circumferentially extending portion of the guide slot 543. The protrusion 541 and the circumferentially-extending portion 543 of the guide slot 540 constrain the axial movement of the actuation member 527 relative to the body 301. In the example of FIGS. 5A to 5E the circumferentially-extending portion 543 is orthogonal or substantially orthogonal to the longitudinal axis of the body 336.

When the guide protrusion 541 is in the circumferentially extending portion of the guide slot 543, the protrusion 531 on the transfer member 533 is in the circumferentially-extending portion 534 of the drive slot. Proximal movement of the transfer member 533 towards the retracted position is translated into rotation of the actuation member 527 relative to the body 301. Rotation of the actuation member 527 moves the protrusion 531 into the second axially-extending portion of the drive slot 535 as shown, for example, in FIG. 5D. As noted, the protrusion 541 and the circumferentially-extending portion 543 of the guide slot 540 constrain the axial movement of the actuation member 527 relative to the body 301.

The guide slot 540 has a second axially-extending portion 546 connected to a second end 545 of the circumferentially extending portion 543 of the guide slot for allowing the actuation member 527 to move distally relative to the body 301. The protrusion 541 and the second axially-extending portion 546 of the guide slot 540 constrain the rotational movement of the actuation member 527 relative to the body 301. The second axially-extending portion 546 of the guide slot is parallel to or substantially parallel to the longitudinal axis of the body 336.

When the actuation member 527 rotates relative to the body 301, the guide protrusion 541 travels along the circumferentially-extending portion of the guide slot 543 to the second axially-extending portion 546 of the guide slot. The actuation member 527 can then be moved distally relative to the body 301 when the guide protrusion 541 is in the second axially-extending portion 546 of the guide slot, as the actuation member 527 moves from the protruded position to the actuation position as shown, for example, in FIG. 5E.

When the actuation member 527 moves from the protruded position to the actuation position, the protrusion 531 travels in the second axially-extending portion of the drive slot 535, and the guide protrusion 541 travels in the second axially-extending portion of the guide slot 546.

If a user removes the transfer member 533 from the injection site while the protrusion 531 is in the circumferentially-extending portion of the drive slot 534, and the guide protrusion 541 is in the first axially-extending portion of the of the guide slot 542 or in the circumferentially-extending portion of the guide slot 543, and if the medicament delivery device has a biasing means for biasing the transfer member 533 towards the extended position, then the biasing means allows the transfer member 533 to return to the extended position upon removal of the device from the injection site. As noted above, the biasing means may be a spring 362.

The guide slot 540 has a diagonally-extending portion 547 connecting the second axially-extending portion 546 to the first axially-extending portion 542 of the guide slot for allowing the guide protrusion 541 to return to the first axially-extending portion and the transfer member 333 to return to the extended position.

If a user removes the transfer member 533 from the injection site while the protrusion 541 is in the second axially-extending portion of the guide slot 546 and before the actuation member 527 has been moved from the protruded position to the actuation position, then the biasing means returns the transfer member 533 to the extended position upon removal of the device from the injection site. The protrusion 541 will travel from the second axially-extending portion of the guide slot 546 to the first axially-extending portion of the guide slot 542 along the diagonally-extending portion 547 or the protrusion 541 will travel from the second axially-extending portion of the guide slot 546 to the first axially-extending portion of the guide slot 542 along the circumferentially-extending portion of the guide slot 543, depending upon the movement of the actuation member 527. For example, if the actuation member 527 moves distally relative to the body 301 first then the guide protrusion 541 will travel along the diagonally-extending portion 547 of the guide slot, and if the actuation member 527 rotates relative to the body 301 first then the guide protrusion 541 will travel along the circumferentially-extending portion 543 of the guide slot to return to the first axially-extending portion of the drive slot 542.

The provision of the diagonally-extending portion 547 of the drive slot is optional although it may improve the reliability of the device by ensuring that the guide protrusion 541 can always return to the first axially-extending portion of the guide slot 542, and hence that the actuation member 527 can always return to the initial position if the transfer member 533 is removed from the injection site before the actuation member 527 has been moved from the protruded position to the actuation position.

The protrusion 531 is at the proximal end of the transfer member 533. In some embodiments, the protrusion may be located distally from the proximal end of the transfer member 533.

In the example of FIGS. 5A to 5E, the protrusion 531 is provided on the transfer member 533 and the drive slot 532 is provided on the actuation member 527. However, in some embodiments, the protrusion 531 is provided on the actuation member 527 and the drive slot 532 is provided on the transfer member 533.

In use, a user places the distal end of the transfer member 533 against an injection site to move the transfer member 533 from the extended position to the retracted position. The protrusion 531 on the transfer member 533 moves proximally within the first axially-extending portion of the drive slot 536 until it reaches the abutment surface 548 in the circumferentially-extending portion 534 of the drive slot. The guide protrusion 541 is in the first axially-extending portion of the guide slot 542. The engagement of the protrusion 531 with the abutment surface 548 transfers proximal movement of the transfer member 533 into proximal movement of the actuation member 527.

Figure 5B:
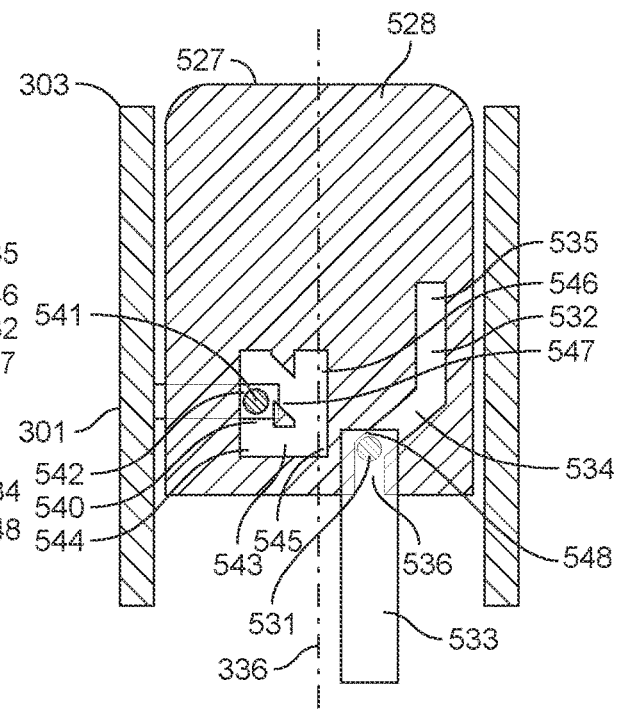
FIG. 5B is a schematic view of the device of FIG. 5A as the transfer member moves from the extended position towards the retracted position.
Figure 5C:
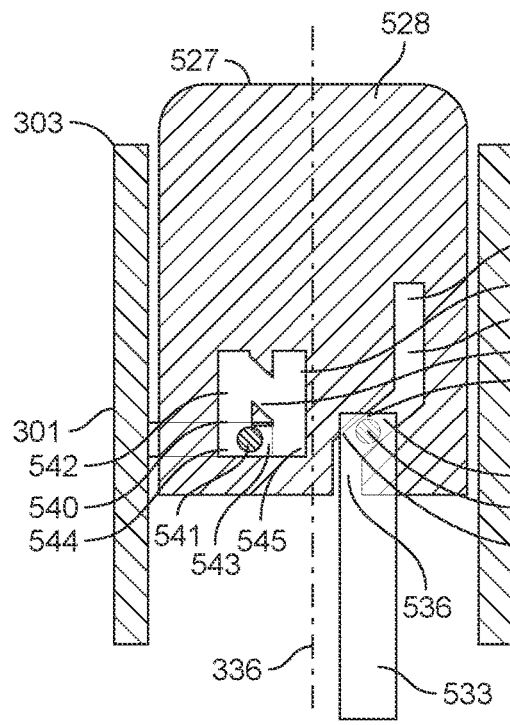
FIG. 5C is a schematic view of the device of FIG. 5A as the transfer member moves from the extended position towards the retraced position.
Figure 5D:
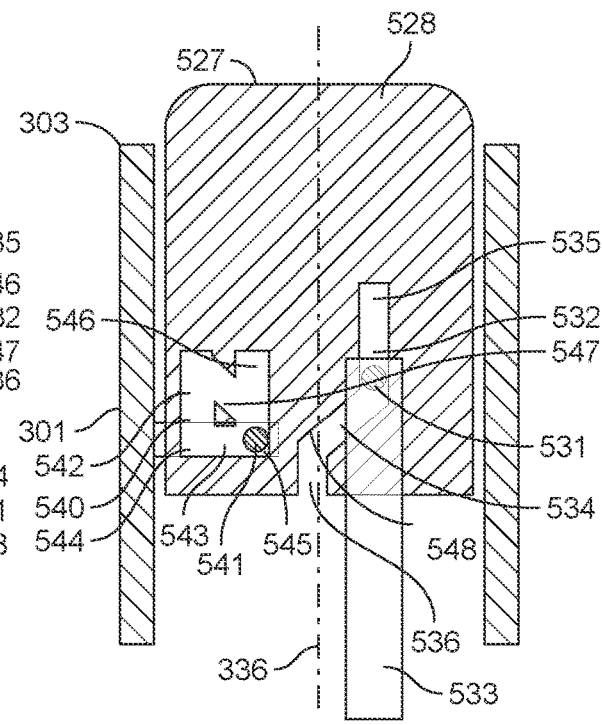
FIG. 5D is a schematic view of the device of FIG. 5A with the actuation member in the protruded position and the protrusion in the axially-extending slot.
Figure 5E:
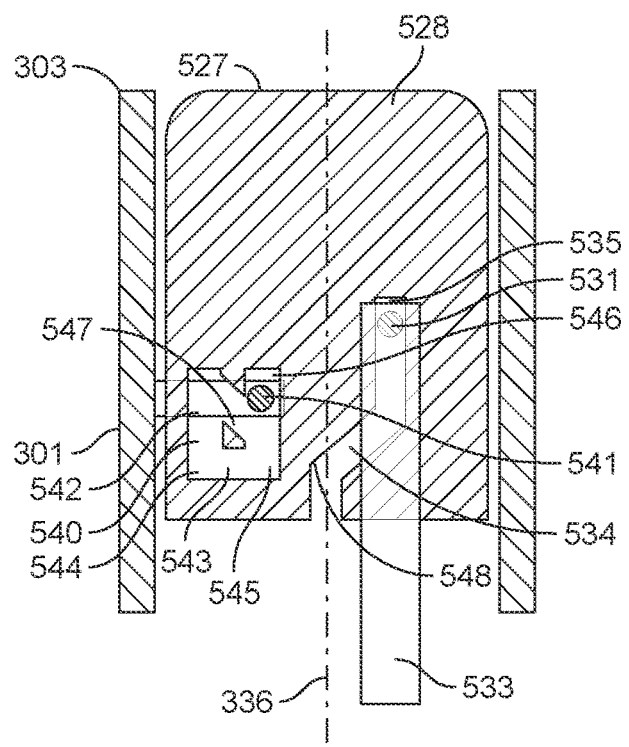
FIG. 5E is a schematic view of the device of FIG. 5A with the actuation member in the actuation position.

As the protrusion 531 engages the abutment surface 538, and moves proximally, the guide protrusion 541 travels axially in the first axially-extending portion of the guide slot 542 as shown, for example in FIG. 5B.

When the guide protrusion 541 reaches the circumferentially-extending portion of the guide slot 543, the protrusion 531 is engaged with a surface of the circumferentially-extending portion of the drive slot 543 but axial movement of the actuation member 527 is restricted relative to the body 301 since the guide protrusion 541 is in the circumferentially-extending portion of the guide slot 543. Since the circumferentially-extending portion of the drive slot 534 has an axial component of direction, proximal movement of the transfer member 533 is transferred into rotation of the actuation member 527 relative to the body 301. The protrusion 531 travels along the circumferentially-extending portion of the drive slot 534 as the transfer member 533 moves proximally until it reaches the second axially-extending portion of the drive slot 535. At this point, the guide protrusion 541 reaches the second axially-extending portion of the guide slot 546.

A user can then move the actuation member 527 distally relative to the body 301 from the protruded position to the actuation position for causing the needle to move from the pre-use position to the injecting position. If the actuation member 527 comprises a button 528 then a user presses the button 528 towards the body 301 to move the actuation member distally relative to the body 301. When the actuation member moves from the protruded position to the actuation position then the needle is caused to move from the pre-use position to the injecting position, for example by the actuation member activating a mechanism for automatically moving the needle from the pre-use position to the injecting position, as described, for example, in relation to the medicament delivery device 300.

Figure 6A:
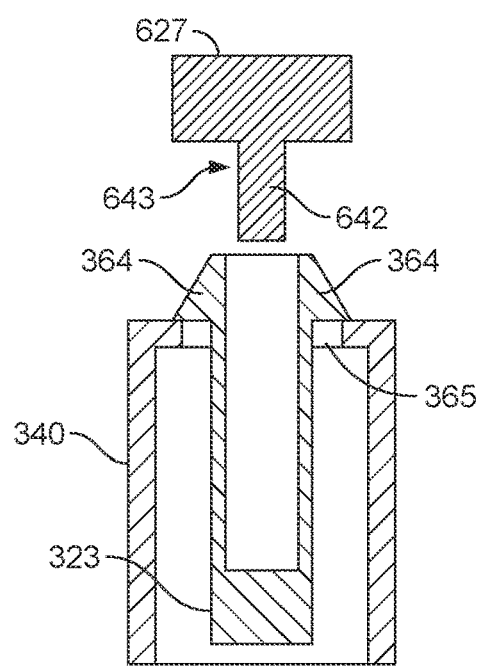
FIG. 6A is a schematic view of part of a mechanism for automatically moving the needle from the pre-use position to the injecting position.
Figure 6B:
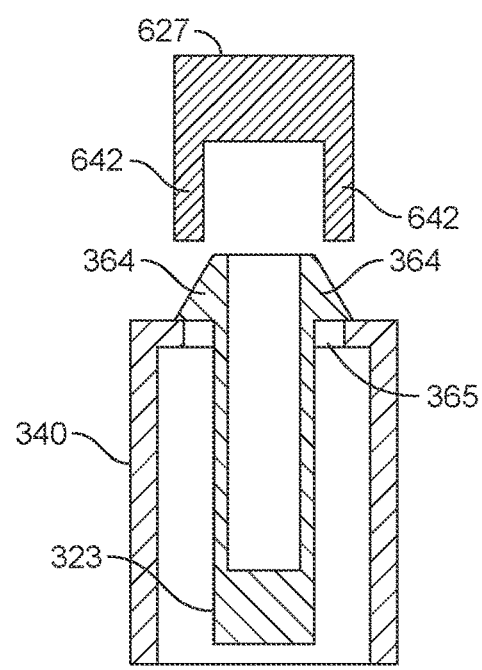
FIG. 6B is a schematic view of FIG. 6A with the actuation member rotated.
Figure 6C:
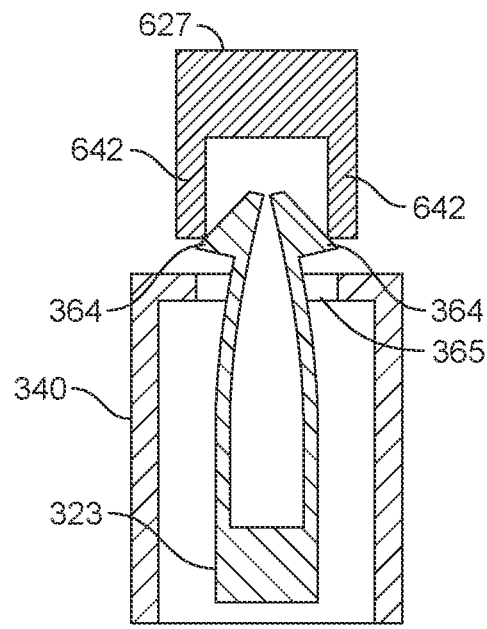
FIG. 6C is a schematic view of FIG. 6A with the actuation member in the actuation position.

FIGS. 6A to 6C show details of part of an example of a mechanism for automatically moving the needle from the pre-use position to the injecting position. This mechanism can be used with any of the features of the medicament delivery devices described herein. The mechanism of FIGS. 6A to 6C has corresponding features to the mechanism as shown and described above in relation to FIGS. 3A to 3D, and can be used in combination with some or all of the features described in relation to 3A to 3D, FIGS. 4A to 4D and 5A to 5E.

The mechanism for automatically moving the needle from the pre-use position to the injecting position has a spring and a plunger 323 which is biased distally by the spring, as discussed above in relation to FIGS. 3A to 3D, for example. When the actuation member 627 is in the actuation position the spring is released to move the plunger 323 distally from a proximal position to a distal position, thereby causing the needle to move from the pre-use position to the injecting position.

The plunger 323 comprises proximally-extending flexible clips 364.

The actuation member 627 comprises a firing boss 643 for engaging the flexible clips 364 to activate the mechanism for automatically moving the needle from the pre-use position to the injecting position. The firing boss 643 comprises protrusions 642 for engaging the proximally-extending flexible clips 364. The actuation member 627 is rotatable relative to the body in order to align the protrusions 642 with the clips 364 for engaging the mechanism.

The actuation member 627 is rotatable from a first position in which the protrusions 642 are not axially aligned with the proximally-extending flexible clips 364 as shown, for example, in FIG. 6A, to a second position in which the protrusions 642 are axially aligned with the proximally-extending flexible clips 364 as shown, for example, in FIG.

6B. The actuation member 627 may be rotated relative to the body, as discussed above in relation to FIGS. 4A to 4D, and 5A to 5E, for example.

In some embodiments, when the actuation member 627 is in the first position, it is not possible to activate the mechanism since the protrusions 642 are not axially aligned with the proximally-extending flexible clips 364. In such embodiments, the protrusions 642 cannot engage the proximally-extending flexible clips 364 if the actuation member 627 is moved distally from a protruded position to the actuation position.

In contrast, when the actuation member 627 is in the second position, the mechanism can be activated by moving the actuation member 627 distally since the protrusions 642 are axially aligned with the proximally-extending flexible clips 364. The protrusions 642 engage the proximally-extending flexible clips 364 when the actuation member is moved from the protruded position as shown, for example, in FIG. 6B, to the actuation position as shown, for example, in FIG. 6C.

The medicament delivery device comprises an inner body 340 which contains at least part of the mechanism for automatically moving the needle from the pre-use position to the injecting position.

The one or more clips 364 protrude through an opening 365 in the proximal end of the inner body. The one or more clips 364 engage with the inner body 340 for maintaining the plunger 323 in the proximal position. Alternatively, the one or more clips may engage with another component of the device.

When the protrusions 642 engage with the proximally-extending flexible clips 364, as shown for example in FIG. 6C, the protrusions 642 flex the proximally-extending clips radially-inwardly. This allows the clips 364 to move distally through the opening 365, thereby releasing the spring.

As discussed above, the device comprises a syringe 350 for containing medicament. The syringe comprises the needle. The plunger 323 is connected to the syringe. When the spring is released, the plunger 323 moves the syringe distally. The plunger 323 also move distally within the syringe for dispensing medicament via the needle. Alternatively, the plunger may only perform one of the actions of moving the syringe distally or moving distally within the syringe for dispensing medicament via the needle.

Figure 7:
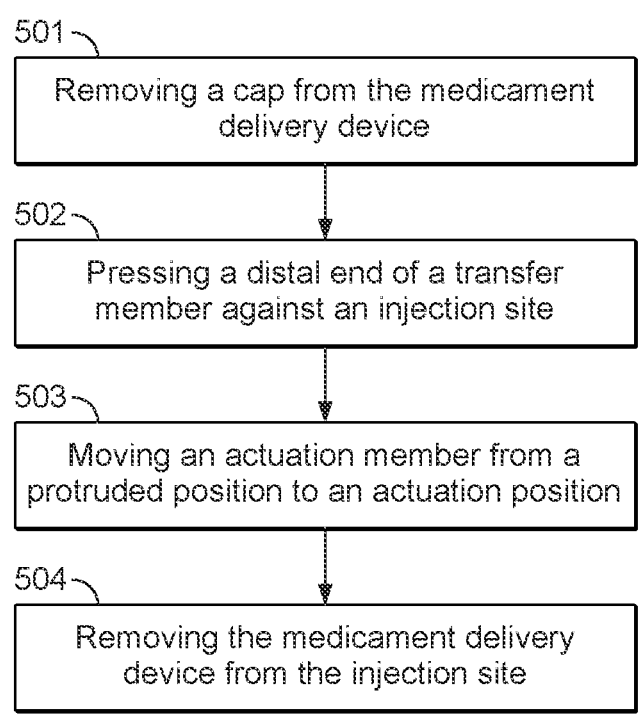
FIG. 7 is a flow chart of a method in accordance with one or more embodiments disclosed herein.

FIG. 7 is a flow chart of a method in accordance with one or more embodiments.

In a first step 501, the method includes removing a cap from the medicament delivery device. The medicament delivery device may have any of the features of the medicament delivery devices described herein.

In a subsequent step 502, the method includes pressing a distal end of a transfer member against an injection site. Pressing the distal end of a transfer member against an injection site moves the transfer member relative to a body from an extended position to a retracted position.

In a subsequent step 503, the method includes moving an actuation member from a protruded position to an actuation position. Moving the actuation member from the protruded position to the actuation position activates a mechanism which automatically moves a needle from a pre-use position, in which the distal end of the needle is located within the body, to an injecting position in which the distal end of the needle protrudes outside of the body for injecting medicament.

Optionally, the method may include rotating the actuation member relative to the body before the step 503 of moving the actuation member from the protruded position to the actuation position.

In a subsequent step 504, the method includes removing the medicament delivery device from the injection site.

The inclusion of the cap, and hence method step 501, is optional.

The medicament delivery device may have any of the features as described or contemplated herein. The method may include additional steps as described or contemplated herein.

LIST OF FEATURES

- 10—device
- 11—body
- 12—cap
- 13—needle sleeve
- 17—needle
- 20—distal region
- 21—proximal region
- 22—button
- 23—piston
- 200—medicament delivery device
- 201—body
- 202—distal end of the body
- 203—proximal end of the body
- 208—locking member
- 216—lock ring
- 217—needle
- 223—plunger
- 228—button
- 232—injection site
- 250—syringe
- 254—cap
- 260—spring
- 262—spring
- 300—medicament delivery device
- 301—body
- 302—distal end of the body
- 303—proximal end of the body
- 317—needle
- 318—distal end of needle
- 320—cap
- 323—plunger
- 327—actuation member
- 328—button
- 329—proximal end of button
- 332—injection site
- 333—transfer member
- 336—longitudinal axis of the body
- 340—inner body
- 341—distal end of transfer member
- 342—protrusion
- 343—firing boss
- 350—syringe
- 360—spring
- 362—spring
- 363—mechanism for automatically moving the needle from the pre-use position to the injecting position
- 364—clip
- 365—proximal opening
- 427—actuation member
- 428—button
- 431—protrusion
- 432—drive slot 433—transfer member
434—circumferentially-extending portion of drive slot
435—axially-extending portion of drive slot
448—abutment surface
501—method step
502—method step
503—method step
504—method step
527—actuation member
528—button
531—protrusion
532—drive slot
533—transfer member
534—circumferentially-extending portion of drive slot
535—axially-extending portion of drive slot
536—axially extending portion of drive slot
540—guide slot
541—guide protrusion
542—axially-extending portion of guide slot
543—circumferentially-extending portion of guide slot
544—first end
545—second end
546—axially-extending portion of guide slot
547—diagonally-extending portion of guide slot
548—abutment surface
627—actuation member
642—protrusion
643—firing boss The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly (A21), Arg (B31), Arg (B32) human insulin (insulin glargine); Lys (B3), Glu (B29) human insulin (insulin glulisine); Lys (B28), Pro (B29) human insulin (insulin lispro); Asp (B28) human insulin (insulin as part); human insulin, proline in position B28 is replaced by Asp, Lys, Leu, Val or Ala and in position B29 Lys may be replaced by Pro; Ala (B26) human insulin; Des (B28-B30) human insulin; Des (B27) human insulin and Des (B30) human insulin.

Examples of insulin derivatives are, for example, B29-N-myristoyl-des (B30) human insulin, Lys (B29) (N-tetradecanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N—(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F (ab) and F (ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the devices and methods disclosed herein include, for example, Fab fragments, F (ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014 (E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014 (E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014 (E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The invention claimed is:

1. A medicament delivery device comprising:
a body having a proximal end and a distal end;
a needle configured to be movable relative to the body from a pre-use position in which a distal end of the needle is located proximal to the distal end of the body to (ii) an injection position in which the distal end of the needle is distal to the distal end of the body for injecting a medicament;
an actuation member configured to be movable proximally relative to the body from (i) an initial position to (ii) a protruded position in which a proximal end of the actuation member protrudes from the proximal end of the body to (iii) an actuation position, the medicament delivery device being configured such that moving the actuation member distally relatively to the body from the protruded position to the actuation position moves the needle from the pre-use position to the injection position; and
a transfer member configured to move the actuation member from the initial position to the protruded position, the transfer member being movable relative to the body between (i) an extended position in which a distal end of the transfer member protrudes from the distal end of the body and (ii) a retracted position in which the transfer member is located proximally from the extended position,
wherein one of the actuation member or the transfer member comprises a protrusion and the other of the actuation member or the transfer member comprises a drive slot, the protrusion configured to be located in the drive slot for limiting movement of the transfer member relative to the actuation member, the drive slot comprising a circumferentially-extending portion comprising an abutment surface, and the medicament delivery device being configured such that the protrusion engages the abutment surface when the transfer member moves from the extended position towards the retracted position to move the actuation member from the initial position to the protruded position.

2. The medicament delivery device of claim 1, wherein the drive slot comprises an axially-extending portion for allowing the actuation member to move axially relative to the transfer member when the protrusion is located in the axially-extended portion and when the actuation member moves from the protruded position to the actuation position.

3. The medicament delivery device of claim 2, wherein the actuation member is rotatable by a user relative to the body when the actuation member is in the protruded position to move the protrusion from the circumferentially-extending portion of the drive slot to the axially-extending portion of the drive slot.

4. The medicament delivery device of claim 1, wherein the circumferentially-extending portion is orthogonal or substantially orthogonal to a longitudinal axis of the body.

5. The medicament delivery device of claim 1, comprising a mechanism for automatically moving the needle from the pre-use position to the injection position, the mechanism configured to be activated by moving the actuation member from the protruded position to the actuation position.

6. The medicament delivery device of claim 5, wherein the actuation member comprises a boss for engaging a part of the mechanism to activate the mechanism.

7. The medicament delivery device of claim 6, wherein the boss comprises one or more protrusions for engaging the part of the mechanism to activate the mechanism, wherein the medicament delivery device is configured such that rotation of the actuation member relative to the body moves the one or more protrusions from a first position in which the one or more protrusions are not axially aligned with the part of the mechanism to a second position in which the one or more protrusions are axially aligned with the part of the mechanism.

8. The medicament delivery device of claim 6, wherein the medicament delivery device is configured such that the mechanism is not activated by moving the transfer member from the extended position to the retracted position.

9. The medicament delivery device of claim 1, wherein the circumferentially-extending portion of the drive slot has an axially-extending component of direction for translating axial movement of the protrusion into rotation of the actuation member relative to the body.

10. The medicament delivery device of claim 9, wherein one of the actuation member or the body or a component which is fixed relative to the body comprises a guide slot, and the other of the actuation member or the body or the component which is fixed relative to the body comprises a guide protrusion, the guide protrusion being located in the guide slot for limiting movement of the actuation member relative to the body.

11. The medicament delivery device of claim 10, wherein the guide slot comprises a circumferentially-extending portion for permitting rotation of the actuation member relative to the body.

12. The medicament delivery device of claim 10, wherein the guide slot comprises an axially-extending portion, and the medicament delivery device is configured such that when the protrusion engages the abutment surface, the guide protrusion is located in the axially-extending portion for allowing the actuation member to move axially relative to the body when the transfer member moves from the extended position towards the retracted position.

13. The medicament delivery device of claim 12, wherein the guide slot comprises a circumferentially-extending portion for allowing rotation of the actuation member relative to the body, the circumferentially-extending portion of the guide slot having a first end connected to the axially-extending portion of the guide slot, and the medicament delivery device configured such that when the transfer member moves from the extended position towards the retracted position, the guide protrusion travels from the axially-extending portion of the guide slot to the circumferentially extending portion of the guide slot.

14. The medicament delivery device of claim 13, wherein the axially-extending portion of the guide slot is a first axially-extending portion, and the guide slot further comprises a second axially-extending portion connected to a second end of the circumferentially extending portion of the guide slot for allowing the actuation member to move axially relative to the body when the actuation member moves from the protruded position to the actuation position.

15. The medicament delivery device of claim 14, wherein the guide slot comprises a diagonally-extending portion connecting the second axially-extending portion to the first axially-extending portion for allowing the guide protrusion to return to the first axially-extending portion of the guide slot and the transfer member to return to the extended position.

16. The medicament delivery device of claim 1, further comprising a biasing member for biasing the transfer member in a direction from the retracted position towards the extended position.

17. The medicament delivery device of claim 16, wherein the biasing member comprises a spring.

18. The medicament delivery device of claim 1, further comprising a cap configured to be removably attachable to the body, the cap configured to cover the distal end of the transfer member for limiting the transfer member being moved from the extended position to the retracted position when the cap is attached to the body.

19. The medicament delivery device of claim 1, further comprising a lock ring configured to be rotatable from (i) a first lock ring position in which the lock ring limits movement of the actuation member from the protruded position towards the actuation position to (ii) a second lock ring position in which the lock ring allows movement of the actuation member from the protruded position towards the actuation position.

20. The medicament delivery device of claim 1, wherein the actuation member comprises a button configured to be pressed by a user to move the actuation member from the protruded position to the actuation position.

21. The medicament delivery device of claim 20, wherein the medicament delivery device is configured such that when the actuation member is in the initial position, a proximal end of the button is substantially flush with the proximal end of the body.

22. The medicament delivery device of claim 20, wherein the medicament delivery device is configured such that when the actuation member is in the initial position, a proximal end of the button is located distally from the proximal end of the body.

23. The medicament delivery device of claim 1, wherein the medicament delivery device comprises a syringe containing medicament and comprising the needle.

24. A method comprising:
moving a distal end of a transfer member of a medicament delivery device proximally relative to a body of the medicament delivery device from (i) an extended position in which the distal end of the transfer member protrudes distally from a distal end of the body to (ii) a retracted position such that movement of the transfer member from the extended position to the retracted position moves an actuation member of the medicament delivery device proximally relative to the body from (i) an initial position to a (ii) protruded position,
wherein the actuation member is movable distally relative to the body from the protruded position to an actuation position for moving a needle from (i) a pre-use position in which a distal end of the needle is proximal to the distal end of the body to (ii) an injection position in which the distal end of the needle is proximal to the distal end of the body.

25. The method of claim 24, further comprising rotating the actuation member relative to the body.

26. The method of claim 25, wherein rotating the actuation member relative to the body comprises rotating the actuation member when the actuation member is in the protruded position.

27. The method of claim 25, wherein rotating the actuation member relative to the body comprises the transfer member rotating the actuation member when the transfer member moves from the extended position to the retracted position.

28. A method comprising:
pressing a distal end of a transfer member of a medicament delivery device against an injection site to move the transfer member relative to a body of the medicament delivery device from an extended position to a retracted position to move an actuation member of the medicament delivery device relative to the body from an initial position to a protruded position; and
moving the actuation member distally relative to the body from the protruded position to an actuation position.

29. The method of claim 28, further comprising rotating a lock ring from (i) a first lock ring position in which the lock ring limits movement of the actuation member from the protruded position towards the actuation position to (ii) a second lock ring position in which the lock ring allows movement of the actuation member from the protruded position towards the actuation position.

* * * * *

UNITED STATES PATENT AND TRADEMARK OFFICE
CERTIFICATE OF CORRECTION

PATENT NO. : 12,377,226 B1
APPLICATION NO. : 18/640710
DATED : August 5, 2025
INVENTOR(S) : Alexander Hee-Hanson and Michael Parrott Page 1 of 1

It is certified that error appears in the above-identified patent and that said Letters Patent is hereby corrected as shown below:

In the Claims

Column 27, Line 26, Claim 1, after "from", insert -- (i) --

Signed and Sealed this
Twenty-first Day of October, 2025

John A. Squires
*Director of the United States Patent and Trademark Office*